US00PP24740P3

(12) United States Plant Patent
Jensen

(10) Patent No.: US PP24,740 P3
(45) Date of Patent: Aug. 5, 2014

(54) ***CAMPANULA* PLANT NAMED 'B.10.082'**

(50) Latin Name: ***Campanula portenschlagiana* Schult.**
Varietal Denomination: B.10.082

(75) Inventor: Gert Kim Jensen, Marslev (DK)

(73) Assignee: Rosa-Danica A/S, Marslev (DK)

( * ) Notice: Subject to any disclaimer, the term of this patent is extended or adjusted under 35 U.S.C. 154(b) by 118 days.

(21) Appl. No.: 13/506,927

(22) Filed: May 25, 2012

(65) Prior Publication Data

US 2013/0318670 P1 Nov. 28, 2013

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from Community Plant Variety Office (CPVO) website for corresponding CPVO application No. 2012/0608 filed Mar. 13, 2012 (1 page) (http://www.cpvoextranet.cpvo.europa.eu).
Printout of application information for Canadian Plant Breeders' Rights application No. 12-7587 filed Apr. 10, 2012, published in Plant Varieties Journal No. 84, Jul. 31, 2012 (1 page) (vvww.inspection.gc.ca/plants/plant-breeders-rights/plant-varieties-joumal).

*Primary Examiner* — Wendy C Haas
(74) *Attorney, Agent, or Firm* — Foley & Lardner LLP

(57) ABSTRACT

A new and distinct cultivar of *Campanula* plant named 'B.10.082', characterized by its compact upright plant habit; dense and bushy plant form; vigorous growth habit; and large upright, violet flowers.

2 Drawing Sheets

Latin name of the genus and species of the claimed plant: *Campanula portenschlagiana* Schult.

Variety denomination: 'B.10.082'.

BACKGROUND OF THE INVENTION

The present invention relates to a new and distinct cultivar of *Campanula* plant, botanically known as *Campanula portenschlagiana* Schult., commonly known as Dalmatian Bellflower and hereinafter referred to by the cultivar name 'B.10.082'.

The new *Campanula* cultivar is a product of a planned breeding program conducted by the inventor, Gert Jensen, in Marslev, Denmark.

The new *Campanula* originated from a selfing cross made in 2010 by the Inventor between plants of the *Campanula portenschlagiana* Schult. variety 'B.09.01' (U.S. Plant Pat. No. 23,876). The Inventor selected the new *Campanula* cultivar from the progeny of the above crossing in 2011 on the basis of its compact, upright growth, with low need for retardation and fungicides and distinctive flowering habit.

Asexual reproduction of the new *Campanula* cultivar by terminal vegetative cuttings in Marslev, Denmark has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'B.10.082', which in combination distinguish this *Campanula* as a new and distinct cultivar:

1. Violet, single bell flowers;
2. High numbers of flowers per plant;
3. Dense and bushy plant form, mainly due to more upright stems;
4. Upright plant habit;
5. Less need for growth retardant.

Plants of the cultivar 'L 10.018' can be compared to plants of the *Campanula portenschlagiana* Schult. cultivar 'B.09.01' (U.S. Plant Pat. No. 23,876). However, in side-by-side comparisons conducted by the Inventor in Marslev, Denmark, plants of the cultivar 'B.10.082' and the cultivar 'B.09.01' differ in the following characteristics, it must however be mentioned that the new cultivar plant examined has not been treated with growth retardant.

1. Plants of the new *Campanula* have violet, single bell, upright flowers compared to the deep violet flowers of 'B.09.01'.
2. Plants of the new *Campanula* have more upright growth than plants of the cultivar 'B.09.01'.
3. Plants of the new *Campanula* do not need growth retardant or cooling treatment.
4. Plants of the new *Campanula* have smaller leaves and thus less conspicuous foliage when flowering.
5. Plants of the new *Campanula* have more flowers per plant than the plants of the cultivar 'B.09.01'.
6. Plants of the new *Campanula* appears to be less susceptible to grey mold (*Botrytis cinerea*).
7. Plants of the new *Campanula* have a shorter production time than the plants of the cultivar 'B.09.01'.

BRIEF DESCRIPTION OF THE PHOTOGRAPHS

The accompanying photographs illustrate the overall appearance of the new *Campanula* 'B.10.082' showing the colors as true as is reasonably possible with colored reproductions of this type. Colors in the photographs may differ slightly from the color value cited in the detailed botanical description, which accurately describe the color of 'B.10.082'.

DETAILED BOTANICAL DESCRIPTION

Figure 1:
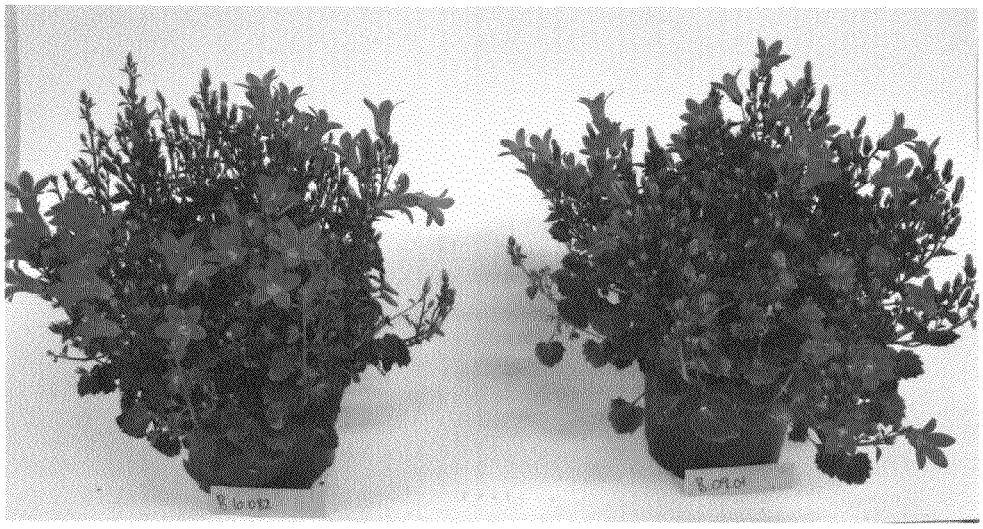
FIG. 1 shows a side perspective view of a typical flowering plant of 'B.10.082' compared to a typical flowering plant of 'B.09.01' grown in 10.5 cm pots.
Figure 2:
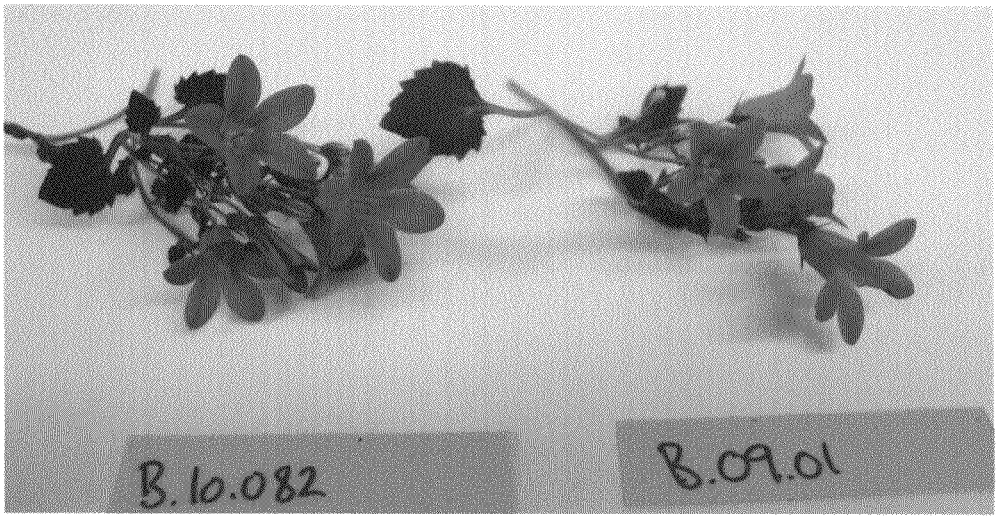
FIG. 2 shows a close-up view of typical single flowers of 'B.10.082' along with typical single flowers of 'B.09.01'.

The new *Campanula* 'B.10.082' has not been observed under all possible environmental conditions. The phenotype of the new cultivar may vary with variations in environment such as temperature, light intensity, and day length without any change in the genotype of the plant.

In the following description, color references are made to The Royal Horticultural Society Colour Chart, 4$^{th}$ edition, where general terms of ordinary dictionary significance are used. Plants were grown under greenhouse conditions with an average day temperature of 18-20° C., an average night temperature of 16° C., ambient (60 watt) light level, and 6 weeks of long day treatments (16 hrs). Plants used for this description were grown for about 14 weeks after cutting.

Botanical classification: *Campanula portenschlagiana* Schuh cultivar 'B.10.082'.

Parentage:

*Female parent.*—*Campanula portenschlagiana* Schult, 'B.09.01'.

*Male parent.*—*Campanula portenschlagiana* Schult, 'B.09.01'.

Propagation:

*Type cutting.*—Terminal vegetative cuttings.

*Time to initiate roots.*—About 10 to 14 days at 18 to 21 C in tunnels in a greenhouse.

*Root description.*—Fine, well branched.

Plant description:

*Form.*—Perennial plant with an upright globular plant habit. Campanulate flowers in racemes. Freely branching with lateral branches forming at every node; dense and bushy. Freely branching, somewhat brittle stems.

*Crop time.*—After rooting, about 13 weeks in long days are required to produce finished flowering plants in 11 cm pots.

*Plant height* (*soil level to top of plant plane*).—About 14 cm.

*Plant diameter.*—18 cm.

*Vigor.*—Vigorous growth rate.

Foliage description: Leaves alternate, single, dentate, palmate (actinodromus), not very conspicuous venation.

*Basal leaves.*—Length: 17-22 mm. Width: About 22 mm. Shape: Cordate. Apex: acuminate. Base: Cordate. Margin: broadly dentate. Texture: smooth, glabrous, dull. Color: Young foliage, upper and lower surfaces respectively: RHS 139 A and B, green. Mature foliage, upper and lower surfaces respectively: RHS 147A, and 138A, green. Venation, RHS 147C.

*Petioles.*—Length on basal leaves: 3.5 cm. Length on apical leaves 0-12 mm. Diameter: 1.0 mm. Color: RHS N138D.

Flower description:

*Flower arrangement and shape.*—Single flowers in racemes; Violet campanulate flowers with small star shaped calyx.

*Natural flowering season.*—Continuous throughout the spring and summer in Denmark. Season can be extended by long day treatments. 6 weeks (16 hour) are needed for flower induction under greenhouse conditions.

*Flower longevity on the plant.*—Longevity (9 to 14 days) of individual flowers is highly dependent on temperature and light conditions. Flowers persistent.

*Inflorescence size.*—Length: About 10 cm.

*Number of flowers per inflorescence.*—17-22.

*Flower buds.*—Color: RHS 90B, violet-blue with ridges slightly lighter, RHS 91A. Texture: with ridges. Length: up to 11 mm long and. Width: 4 mm before anthesis.

*Flowers.*—Attitude: Upright. Length (height): About 15 mm. Diameter: About 20 mm. Shape: Broadly arrow-shaped, acuminate.

*Petal lobes.*—Length: 7 mm. Width: 5 mm.

*Corolla tube.*—Color: Upper and lower surfaces, RHS N87C, bottom of bell RHS N87D, maturing to RHS 87C.

Peduncle:

*Strength.*—Moderately strong.

*Length.*—About 13 mm.

*Diameter.*—About 1 mm.

*Color.*—RHS 144B yellow-green

Reproductive organs:

*Stamen.*—Number: 5, fused until pollen has been shed.

*Anther.*—Shape: Fused, after shedding curling. Size: 1 mm. Color: RHS 158B.

*Pollen.*—Amount: Average. Color: RHS 158B.

*Pistil.*—Number: 1. Length: 12 mm.

*Stigma.*—Shape: Tripartite. Color: RHS 85B.

*Style.—Length:* 11 mm. Color: RHS 84C.

*Ovary.*—Color: RHS 150D.

Seeds:

*Quantity.*—20-30 per flower.

*Length.*—1 mm.

Weather tolerance: Plants of the new *Campanula* have not been tested for tolerance to drought, rain and wind, low temperature.

Disease resistance: Plants of the new claimed variety have shown good resistance to grey mold (*Botrytis cinerea*).

What is claimed is:

1. A new and distinct cultivar of *Campanula* plant named 'B.10.082', as illustrated and described herein.

* * * * *